(12) United States Patent
Di Benedetto et al.

(10) Patent No.: US 11,727,817 B2
(45) Date of Patent: Aug. 15, 2023

(54) UNMANNED AERIAL VEHICLE DELIVERY SYSTEM FOR DELIVERY OF MEDICAL OR EMERGENCY SUPPLIES

(71) Applicant: Drone Delivery Canada Corp., Vaughan (CA)

(72) Inventors: Paul Di Benedetto, Vaughan (CA); Gregory Colacitti, Vaughan (CA)

(73) Assignee: Drone Delivery Canada Corp., Vaughan (CA)

(*) Notice: Subject to any disclaimer, the term of this patent is extended or adjusted under 35 U.S.C. 154(b) by 59 days.

(21) Appl. No.: 17/409,951

(22) Filed: Aug. 24, 2021

(65) Prior Publication Data

US 2021/0390869 A1 Dec. 16, 2021

Related U.S. Application Data

(62) Division of application No. 15/796,252, filed on Oct. 27, 2017, now Pat. No. 11,127,305.

(51) Int. Cl.
*G08G 5/00* (2006.01)
*G08G 5/02* (2006.01)
(Continued)

(52) U.S. Cl.
CPC ............. *G08G 5/0069* (2013.01); *A61N 1/39* (2013.01); *B64C 39/024* (2013.01); *B64D 47/08* (2013.01);
(Continued)

(58) Field of Classification Search
CPC .. G08G 5/0069; G08G 5/0013; G08G 5/0026; G08G 5/0034; G08G 5/006;
(Continued)

(56) References Cited

U.S. PATENT DOCUMENTS 5,586,438 A 12/1996 Fahy
6,210,329 B1 4/2001 Christmas et al.
(Continued)

FOREIGN PATENT DOCUMENTS

CN 204368441 U 6/2015
CN 105068486 A 11/2015
(Continued)

OTHER PUBLICATIONS

Written Opinion of the International Searching Authority and International Search Report dated Jan. 16, 2019.
(Continued)

*Primary Examiner* — Truc M Do
(74) *Attorney, Agent, or Firm* — Bereskin & Parr LLP/S.E.N.C.R.L., s.r.l.

(57) ABSTRACT

An emergency or medical package comprising has: a body; attachment fittings, for attachment to complementary fittings of a UAV; and a plurality of compartments for housing medical or emergency supplies, including a compartment for a headset, providing two-way communication between a user of a headset and a person remote from the package, wherein the headset includes at least one camera, providing a video feed, that is sent to a remote person. A method of delivering these supplies and providing control over the use of the supplies provides two-way audio and visual communication between a remote person and the user wearing the headset, whereby the remote person can provide instructions and directions to the user. A method of planning a route for the delivery of a medical or emergency package by UAV, and a method for providing for a delivery of a priority package are also provided.

20 Claims, 9 Drawing Sheets

(51) Int. Cl.
*A61N 1/39* (2006.01)
*B64C 39/02* (2023.01)
*B64D 47/08* (2006.01)
*G05D 1/00* (2006.01)
*B64U 101/60* (2023.01)

(52) U.S. Cl.
CPC .......... *G05D 1/0027* (2013.01); *G08G 5/006* (2013.01); *G08G 5/0013* (2013.01); *G08G 5/0026* (2013.01); *G08G 5/0034* (2013.01); *G08G 5/025* (2013.01); *A61N 1/3904* (2017.08); *B64U 2101/60* (2023.01); *B64U 2201/20* (2023.01)

(58) Field of Classification Search
CPC ........ G08G 5/025; A61N 1/39; A61N 1/3904; B64C 39/024; B64C 2201/128; B64C 2201/146; B64D 47/08; G05D 1/0027
See application file for complete search history.

(56) References Cited

U.S. PATENT DOCUMENTS

| | | |
|---|---|---|
| 7,277,752 B2 | 10/2007 | Matos |
| 7,584,071 B2 | 9/2009 | Lee |
| 8,106,748 B2 | 1/2012 | Lee |
| 8,593,108 B2 | 11/2013 | Ferber et al. |
| 8,948,935 B1 | 2/2015 | Peeters et al. |
| 9,051,043 B1 | 6/2015 | Peeters et al. |
| 9,056,676 B1 | 6/2015 | Wang |
| 9,120,568 B2 | 9/2015 | Herman et al. |
| 9,174,733 B1 | 11/2015 | Burgess et al. |
| 9,179,260 B2 | 11/2015 | Ostrander et al. |
| 9,244,147 B1 | 1/2016 | Soundararajan et al. |
| 9,302,783 B2 | 4/2016 | Wang |
| 9,305,280 B1 | 4/2016 | Berg et al. |
| 9,307,383 B1* | 4/2016 | Patrick .................. B64C 39/024 |
| 9,334,052 B2 | 5/2016 | Pasko et al. |
| 9,357,766 B2 | 6/2016 | Steinman et al. |
| 9,384,668 B2 | 7/2016 | Raptopoulos et al. |
| 9,387,928 B1 | 7/2016 | Gentry et al. |
| 9,429,953 B1 | 8/2016 | Miller et al. |
| 9,527,605 B1 | 12/2016 | Gentry et al. |
| 9,573,684 B2 | 2/2017 | Kimchi et al. |
| 9,536,216 B1 | 3/2017 | Lisso |
| 2003/0233129 A1 | 12/2003 | Matos |
| 2005/0129103 A1 | 6/2005 | Bendell et al. |
| 2005/0154653 A1 | 7/2005 | Jongebloed |
| 2007/0203727 A1 | 8/2007 | Moore |
| 2009/0076368 A1 | 3/2009 | Balas |
| 2009/0108016 A1 | 4/2009 | Brown et al. |
| 2011/0264311 A1 | 10/2011 | Lee et al. |
| 2012/0143482 A1 | 6/2012 | Goossen et al. |
| 2013/0074614 A1 | 3/2013 | Holmes et al. |
| 2014/0032034 A1 | 1/2014 | Raptopoulos et al. |
| 2014/0061273 A1 | 3/2014 | Bullivant |
| 2014/0316243 A1 | 10/2014 | Niedermeyer |
| 2015/0120094 A1* | 4/2015 | Kimchi .................. B64C 39/024 701/3 |
| 2015/0158587 A1 | 6/2015 | Patrick et al. |
| 2015/0336669 A1 | 11/2015 | Kantor et al. |
| 2015/0339933 A1 | 11/2015 | Batla et al. |
| 2015/0353195 A1 | 12/2015 | Peeters et al. |
| 2015/0370251 A1 | 12/2015 | Siegel et al. |
| 2015/0379874 A1 | 12/2015 | Ubhi et al. |
| 2016/0001883 A1 | 1/2016 | Sanz et al. |
| 2016/0016664 A1 | 1/2016 | Basuni |
| 2016/0033966 A1 | 2/2016 | Farris et al. |
| 2016/0096622 A1 | 4/2016 | Richardson |
| 2016/0148495 A1 | 5/2016 | Buchanan |
| 2016/0163204 A1 | 6/2016 | Raptopoulos et al. |
| 2016/0200438 A1 | 7/2016 | Bokeno et al. |
| 2016/0236778 A1 | 8/2016 | Takayama et al. |
| 2016/0244165 A1 | 8/2016 | Patrick et al. |
| 2016/0284221 A1 | 9/2016 | Hinkle et al. |
| 2016/0311532 A1 | 10/2016 | Fleck |
| 2017/0203843 A1 | 7/2017 | Chan et al. |
| 2017/0292757 A1 | 10/2017 | Weaver |
| 2017/0369167 A1* | 12/2017 | Meadow .............. G05D 1/0038 |

FOREIGN PATENT DOCUMENTS

| | | |
|---|---|---|
| CN | 204846372 U | 12/2015 |
| CN | 205169496 U | 4/2016 |
| DE | 102014105583 A1 | 10/2015 |
| DE | 102014213023 A1 | 1/2016 |
| WO | 2007081947 A2 | 7/2007 |
| WO | 2014089083 A1 | 6/2014 |
| WO | 2014170646 A1 | 10/2014 |
| WO | 2015061008 A1 | 4/2015 |
| WO | 2015168573 A1 | 11/2015 |
| WO | 2015175242 A1 | 11/2015 |
| WO | 2016019242 A1 | 2/2016 |
| WO | 2016037219 A1 | 3/2016 |
| WO | 2016094067 A1 | 6/2016 |

OTHER PUBLICATIONS

Dronenet The next Big thing; Global Guerrillas, Wednesday, Jan. 2, 2013.
Toor, "This startup is using drones to deliver medicine in Rwanda", http://theverge.com/1016/4/5/11367274/zipline-drone-delivery-rwanda-medicine-blood, Apr. 5, 2016.
TU Delft, "Ambulance Drone", http://www.io.tudelft.nl/onderzoek/delft-design-labs/applied-labs/ambulance-drone.
Star, "Ambulance drone delivers help to heart attack victims", https://www.cnet.com/news/ambulance-drone-delivery-help-to-heart-attack-victims, Oct. 28, 2014.
International Search Report and Written Opinion in respect of PCT/CA2018/051361 dated Jan. 22, 2019.
Boutilier, J. et al., "Optimizing a drone network to deliver automated external defibrillators". Circulation 2017—The Journal of Emergency Medicine, Sep. 30, 2017 (Sep. 30, 2017), vol. 53, Issue No. 3, pp. 445 and 446.
Dorling, K. et al., "Vehicle Routing Problems for Drone Delivery". IEEE Transactions on Systems, Man, and Cybernetics: Systems, Jan. 1, 2017 (Jan. 1, 2017), vol. 47, Issue No. I,pp. 70 to 85.
Thiels, C. et al., "Use of Unmanned Aerial Vehicles for Medical Product Transport". Air Medical Journal, Mar. 1, 2015 (Mar. 1, 2015), vol. 34, Issue 2, pp. 104 to 108.

* cited by examiner

UNMANNED AERIAL VEHICLE DELIVERY SYSTEM FOR DELIVERY OF MEDICAL OR EMERGENCY SUPPLIES

CROSS-REFERENCE TO RELATED APPLICATION

This application is a division of U.S. application Ser. No. 15/796,252 filed Oct. 27, 2017, the contents of which are incorporated herein by reference. The U.S. application Ser. No. 15/796,252 was filed simultaneously with applicant's application entitled 'Medical or emergency package and method of use thereof', the whole contents of which are incorporated by reference.

FIELD

The present disclosure relates to unmanned aerial vehicles, and more particularly to a method and system for delivery of emergency supplies by an unmanned aerial vehicle.

INTRODUCTION

The following paragraphs are not an admission that anything discussed in them is prior art or part of the knowledge of persons skilled in the art.

Unmanned aerial vehicles (UAVs) have been coming into prominence and have been, in some situations, implemented at consumer levels. An obstacle to expanding the uses of UAVs has been public safety.

Know proposals for using UAVs can be found in U.S. Pat. Nos. 9,174,733 and 9,244,147; and U.S. Publication Nos. 201201453482, 20140032034 and 20150120094, the whole contents of all of which are incorporated by reference. Further, Applicant's earlier application Ser. No. 15/331,147 discloses an unmanned vehicle delivery system and the whole contents of that application are incorporated by reference

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

In accordance with a first aspect of the present disclosure there is provided an emergency or medical package comprising:
a body;
attachment fittings, for attachment to complementary fittings of a UAV; and
a plurality of compartments for housing medical or emergency supplies, including a compartment for a headset, providing two-way communication between a user of a headset and a person remote from the package, wherein the headset includes at least one camera, providing a video feed, that is sent to a remote person.

In accordance with a second aspect of the present disclosure, there is provided a method of delivering a package of emergency medical supplies and providing control over the use of the medical supplies by a remote person, the method comprising:
providing a package of medical supplies, including a headset to be worn by a user, the headset providing for two-way audio and visual communication between a user of the headset at an emergency scene and the remote person;
attaching the package to a UAV and delivering the package by the UAV to a desired location;
at the desired location detaching the package from the UAV and instructing a user at a location to remove the headset from the package; and
providing two-way audio and visual communication between a remote person and the user wearing the headset, whereby the remote person can provide instructions and directions to the user.

In accordance with a third aspect of the present disclosure, there is provided a method of planning a route for the delivery of a medical or emergency package by UAV, and the method comprising:
providing a route network, including a plurality of route sections connected at nodes and connected to UAV zones for UAVs to land and take off;
receiving a request to deliver a medical or emergency package from a departure location to a destination location;
determining if each of the departure location and destination location coincide with one of the UAV zones in the route network;
where the departure and destination locations do coincide with UAV zones to determining a flight route wholly within the flight network;
where at least one of the departure and destination locations is not coincident with one of the UAV zones and is outside of the route network, determining a route extension that provides a connection between that location and the flight route network;
providing regulatory requirements for approval of flight routes;
providing an exemption for delivery of emergency medical packages, requiring a lesser level of approval; and
submitting the flight route for approval, as required.

In accordance with a fourth aspect of the present disclosure, there is provided a method of controlling a plurality of UAVs, the method comprising:
providing a flight control system;
defining a flight route network including a plurality of route sections connecting nodes and UAV zones for landing and taking off of UAVs;
providing at least some route sections with a plurality of corridors for at least one of travel in different directions and at different speeds;
providing for any one UAV to be given priority; and
for each UAV given priority, ensuring that the flight route for that UAV is not obstructed by other UAVs.

In accordance with a fifth aspect of the present disclosure, there is provided a method for providing for a delivery of a priority package, the method comprising:
identifying a location of the package;
identifying UAVs closest to a package, and possible flight routes for each UAV to pick up the package;
determining which UAV will provide for a quickest delivery of the package;
dispatching the selected UAV to pick up the package;
planning a flight route for the selected UAV and the package;
having the UAV pick up the package and sending the UAV along the flight route to the destination location, to deliver the package.

BRIEF DESCRIPTION OF THE FIGURES

For a better understanding of the described embodiments and to show more clearly how they may be carried into effect, reference will now be made, by way of example, to the accompanying drawings in which.

DETAILED DESCRIPTION

Figure 1:
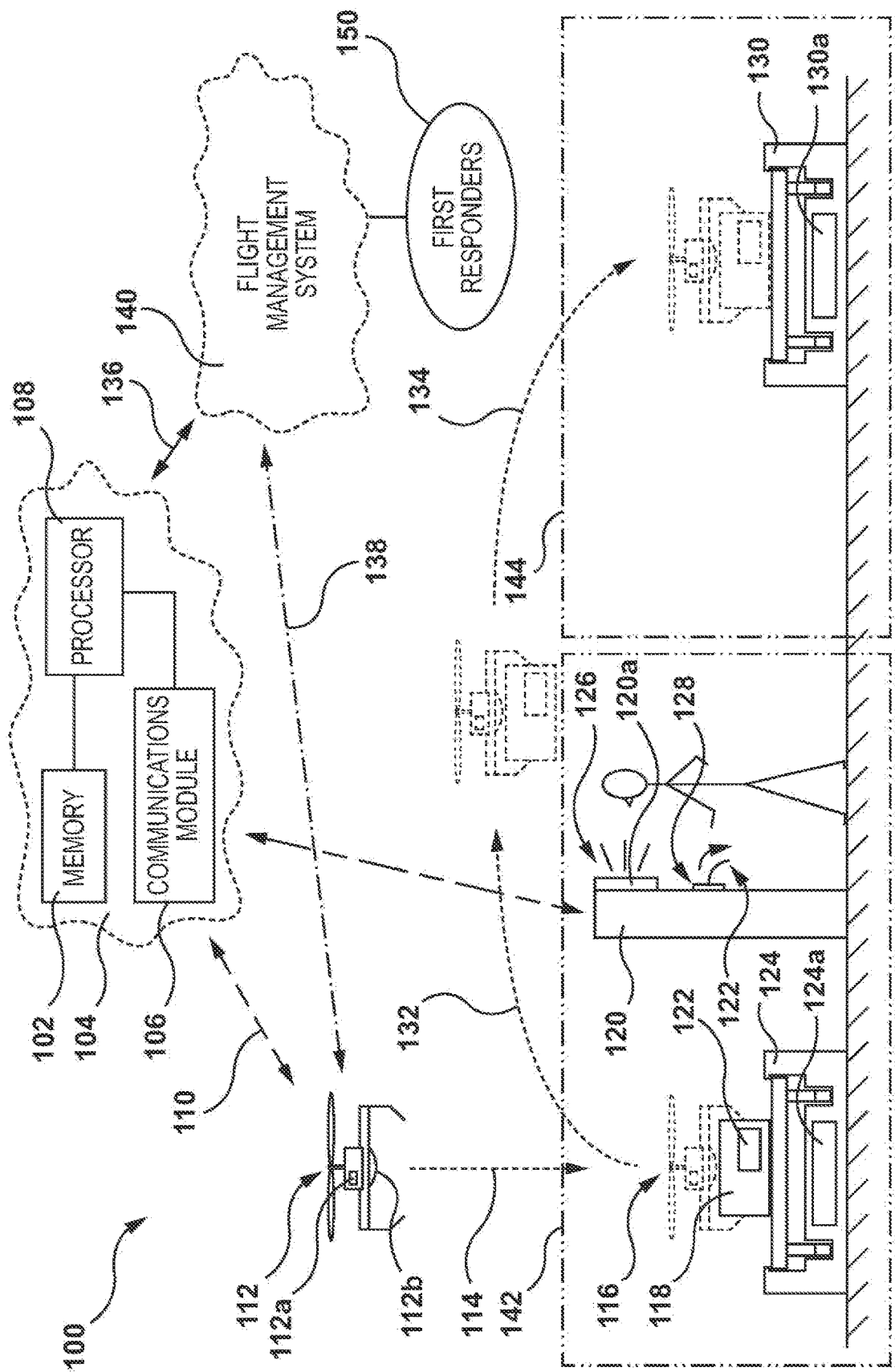
FIG. 1 is a schematic of an example Unmanned Aerial Vehicle (UAV) delivery system.

Various systems, apparatuses or methods will be described below to provide an example of an embodiment of each claimed invention. No embodiment described below limits any claimed invention and any claimed invention may cover apparatuses and methods that differ from those described below. The claimed inventions are not limited to systems, apparatuses and methods having all of the features of any one apparatus or method described below, or to features common to multiple or all of the systems, apparatuses or methods described below. It is possible that a system, apparatus or method described below is not an embodiment of any claimed invention. Any invention disclosed in a system, apparatus or method described below that is not claimed in this document may be the subject matter of another protective instrument, for example, a continuing patent application, and the applicant(s), inventor(s) and/or owner(s) do not intend to abandon, disclaim or dedicate to the public any such invention by its disclosure in this document.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments generally described herein. Furthermore, this description is not to be considered as limiting the scope of the embodiments described herein in any way, but rather as merely describing the implementation of various embodiments as described.

This disclosure includes description of a method and system for delivering an emergency package. The emergency package may be in response to a request for assistance by first responders, and may be labelled or identified as a "first responders" package. It may otherwise be a medical package requiring prompt or emergency delivery and labelled or identified as an "Emergency package". An "Emergency package" may also include non-medical items that require emergency or rapid delivering. Corresponding to the manner in which conventional emergency road vehicle are given priority over other road vehicles, it is anticipated that a UAV delivering a package deemed to be an "emergency" package will be given priority, as detailed below.

UAV DELIVERY SYSTEM OVERVIEW. Reference is now made to FIG. 1, which shows a general purpose unmanned aerial vehicle (UAV) delivery system 10, generally in accordance with Applicant's earlier application Ser. No. 15/331,147 for use with a flight management system 147 for delivering articles 118 between at least a first party and a second party. Such a system is not exclusive to emergency deliveries. Such articles 118 may be referred to as delivery articles 118. The first and second parties may include customers of at least one UAV delivery service. Customers may include, for example, manufacturers, shippers, distributors, or other businesses, and also government agencies. In some cases, customers may have UAV zones 142, 144 at one or more locations, such as locations related to the customers' business(es). A UAV delivery service provider may operate such UAV zones 142, 144 and allow for customers to send delivery articles 118 to and from each other by using UAVs 112 flying between the UAV zones 142, 144.

A UAV delivery service provider may operate such UAV zones 142, 144 by, for example, providing a UAV delivery system 100. As shown in FIG. 1, the UAV delivery system 100 may comprise: a) at least one computing system 104 having a non-transient memory 102 with executable instructions; b) a first UAV zone 142 assigned to a first party; and c) a second UAV zone 144 assigned to a second party. In some cases, the UAV delivery system 100 may also include at least one UAV 112. The flight management system 147 may be provided on the computing system 104.

UAV zones 142, 144 may include features and functionality as described in U.S. Provisional Patent Application No. 62/355,024 and a related utility patent application filed simultaneously with this application, the whole contents of which is hereby incorporated into this document by reference. The computing system 104 may be operable with the UAV zones 142, 144 to provide for UAV 112 deliveries of articles 118 between two or more UAV zones 142, 144—for example, between the first and second UAV zones 142, 144. In some cases, one or more customers may each have more than one UAV zone 142, 144 associated with them or which they may be authorized to use.

Where a package is to be sent by or for first responders, a UAV Zone 142 may be provided at a first responder location, e.g. an ambulance, fire, or police station. It may also be provided at a community center. Alternatively, where such a UAV Zone is not available, or appropriate supply is not available at such a location, a first responders package could be delivered to a conventional UAV Zone 142, 144 as normally used for commercial purposes.

Often, it is expected that a first responders package will be required to be delivered directly to a location where medical emergency has risen, which usually will not be at an established UAV Zone 142, 144. For example, it may be at the scene of a highway accident. There may be cases where first responders package, e.g. a rush delivery of a critical drug, will be required to be delivered to a location, such as a hospital, having an established UAV Zone. In which case, the sequence indicated in FIG. 1 is applicable.

Where a delivery is to be made to other than a known UAV zone, it may be necessary to establish the exact location and coordinates for delivery. In some cases, this may be done by collecting GPS (Global Positioning System) data from mobile telephones or other GPS enabled devices at the location for the delivery. In other cases, it may be possible to provide devices, such as emergency beacons with known coordinates, for communicating information to the location from which a package is to be dispatched.

FUNCTION OF UAV ZONES. In one aspect, the first UAV zone 142 may be operable with the computing system 104 to provide for a takeoff 132 of a UAV 112 from the first UAV zone 142. The second UAV zone 144 may be operable with the computing system 104 to provide for a landing of the UAV 112 in the second UAV zone 144. The computing system 104 may be operable to enable the functionality of the UAV zones 142, 144, including the UAV zones 142, 144 as described in U.S. Patent Application No. 62/355,024.

FUNCTION OF THE FLIGHT MANAGEMENT SYSTEM. The flight management system 147 may control operation of UAVs 112 and may be provided by at least one of a third party and the UAV delivery service provider. Controlling operation of UAVs 112 may include determining UAV 112 availability to carry out one or more requested deliveries of articles 118, determining and arranging for servicing UAVs 112 such as the charging and possibly swapping power sources of UAVs 112, calculating and clearing (for example with one or more transport agencies) flight paths for particular delivery times, and other aspects required for UAV 112 operation. In some examples, the flight management system 147 may be operable to control any one, a combination, or all of UAV 112 takeoffs 132, landings 114, 134, and flights. In other examples, the computing system 104 may be operable with a given flight management system 147 to take over at least one of UAV 132 takeoffs and UAV landings 114, 134 at one or more UAV zones 142, 144 operated at least in part by using that computing system 104. For use by first responders, first responders may have wired and/or wireless link to the Flight Management System 147, as indicated at 150.

THE PORTAL. The computing system 104 may be operable with the instructions (which may be stored on the non-transient memory 102): a) to provide an article delivery portal, the portal being operable to receive at least one delivery request from a first party to deliver at least one article 118 from a first zone 142 to a second zone 144; b) to convert the delivery request into a UAV request; and c) to communicate the UAV request to the flight management system 147. In some examples, the UAV request may include at least: a UAV category request, a timeframe request, an article description, a flight start location, e.g the first zone 142, and a flight end location, e.g. the second zone 144. The article description may include a weight and a set of dimensions of the article 118.

The computing system 104 may be operable with the instructions to receive a response from the flight management system 147, to convert the response into a customer update, and to communicate the update to the portal. The response from to the flight management system 147 may be a response by the flight management system 147 to the UAV request from the computing system 104. The portal may be made available online for various users to access it via any suitable device, including mobile devices such as smart phones. In any case, the portal may include a graphical user interface (GUI).

Further it is possible that communication may be established from a portable or handheld electronic device, such as a smartphone or tablet computer, which could, in effect, provide the functions of the portal. The electronic device can include an app, i.e. an application or program, that will enable communication with the computing system. More particularly, the app may enable communication with emergency first responders. For example, the app my enable a selection between a non-emergency connection to the system 104, and an immediate, emergency connection to first responders, in an analogous way to a 911 call to emergency services. For this purpose, the app may provide for an emergency connection to first responders, to override any security requirements for the electronic device, i.e. there would no requirement to enter a password or biometric identifier (e.g. fingerprint recognition), so that anyone can send a call from an available electronic device.

A call to emergency services through such an app may provide for the emergency responders to ask a series of questions to determine the severity of the situation and what services and equipment is needed. The app may ask questions to determine: if someone has had a heart attack, indicating that an AED is needed; if someone has an allergic reaction or anaphylaxis, indicating that an EpiPen or other device to administer epinephrine or other medication; an overdose of a street drug, indicating that Naloxone or other medication to block the effects of drugs should be administered. These questions and answers can be entered through a touchscreen or other interface and may not require an audio connection.

PORTAL MAY BE PROVIDED VIA A TERMINAL. In some embodiments of the UAV delivery system 100, the portal may be provided via a terminal 120. In one example, the terminal 120 may be weather-proof and may comprise at least one display 120*a*. The display 120*a* may be operable to display the GUI. In some examples, the display 120*a* may include a touch-screen operable to allow a user to input information via the GUI of the portal. In some examples, the terminal 120 may include a keyboard. The portal may be operable to receive communications such as customer updates. In embodiments where the portal may be made available via a terminal 120 having a display 120*a*, the display 120*a* may be operable with the portal to display the communications.

A UAV MAY HAVE A SENSOR AND COMMUNICATIONS MODULE. In embodiments where the UAV delivery system 100 comprises at least one UAV 112, the UAV 112 may have at least one sensor and at least one communications module, and may comprise a display and/or keypad or input device 112*a*. The sensor and communications module may be in communication with a processor and may be operable with the processor to: a) read a unique identifier (in one example, by scanning a hard-copy unique identifier), b) generate a validation signal corresponding to the unique identifier, and c) communicate the validation signal to the computing system 104. At least to minimize physical interaction with the UAV while permitting a user to receive data from and transmit data to the UAV, the UAV, alternatively, may include as part of the communications module, wireless communication, such as Bluetooth to a user's handheld or other device. The processor may be onboard the UAV 102 and may be a remote processor (i.e. external to and lacking physical attachment to the UAV), such as a processor in a cloud-based computing system, in communication with the communication module of the UAV 112.

A USE OF THE VALIDATION SIGNAL. The computing system 104 may be operable to analyze the validation signal in order to ascertain that the delivery article 118 bearing a given unique identifier has been attached to, linked with, or inserted into (depending on the article-retention mechanism of each UAV 112) the UAV 112 assigned to that article (as opposed to a UAV that has not been assigned to that article).

The computing system 104 may be operable with the executable instructions to validate the validation signal and generate a corresponding result, to generate a set of user-instructions based on the result, and to display the set of user-instructions via a display 112a of the UAV 112 to which the article 118 has been attached, linked, or into which the article 118 has been inserted (as applicable, depending on UAV configuration). The set of user-instructions may include at least one of: a) an instruction to reduce the weight of the article 118 by a stated amount, b) an instruction to assign the article 118 to a stated UAV 112, and c) an instruction to position the UAV 112 on a stated UAV zone 142, 144.

As shown in FIG. 2A, a UAV 112 may be provided with attachment fittings 240 that cooperate with attachment fittings 242 or a package. The fittings 242 are mounted on arms 202 of the UAV 200. The fittings 240, 242 can include sensors, that signal that the UAV 200 has been correctly attached to the article 204, which may be desirable, where an inexperienced or untrained person is attaching a package or article 204 to the UAV 200. Additionally, these various fittings can be complementary and compatible between the UAV and different modules that can be assembled to form a package. In our copending application, identified above, there can be provided different modules that are selected and assembled as required, and for delivery by UAV, this may ensure that a package with minimum weight is provided, i.e. by omitting modules that are not required.

DISPLAYING MESSAGES ON A UAV. Depending on the corresponding result, the computing system 104 may be operable to generate and display a confirmation message via, for example, a display 112a of the UAV 112. The computing system 104 may be further operable to generate and display an error message via the display 112a to indicate that the UAV 112 is an incorrect UAV 112. The computing system 104 may be further operable to, concurrently with generating the error message, generate a halt-flight signal for the incorrect UAV 112 and transmit this signal to the flight management system 147 that may be in charge of that UAV 112 during at least a portion of the delivery to be effected by that UAV 112.

Figure 2:
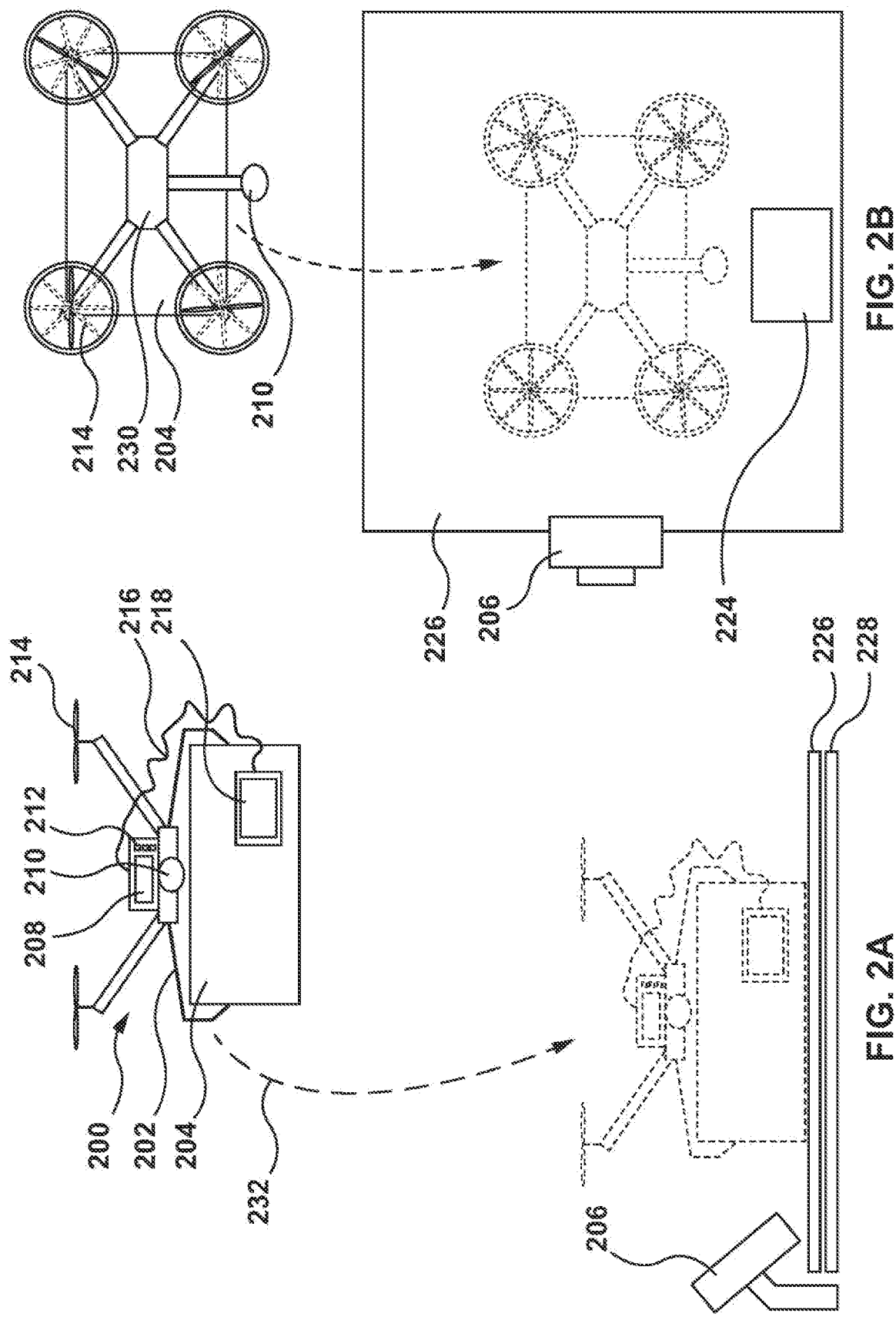
FIGS. 2A and 2B are side view and plan view, respectively, schematics of an example UAV pad for an example UAV, according to one embodiment.

FIG. 2 shows a UAV 200 in further detail, including rotors 214 mounted on arms extending from a main body of the UAV 200. It additionally shows a display and keypad?put device comprising a display 208 and a keypad 212.

QR CODES AND IDENTIFIER-DEVICE. In some cases, unique identifiers may include one or more Quick Response (QR) codes. In such cases, the identifier-device 206 may include a QR code reader operable to read the QR codes to extract the dataset(s) that may be embodied in the QR codes, and to communicate the dataset(s) to at least one of the computing system 104 and the flight management system 147. In one example, an identifier-device 206 may be arranged with a given weight-sensitive UAV pad 226 such that the identifier-device 206 may automatically read a QR code attached to an article 118 in response to the article 118 being placed onto the UAV pad 226.

USER AUTHENTICATION INTO PORTAL. Users of the UAV delivery system 100 may be authenticated to use one or more UAV zones 142, 144, depending on, for example, a subscription of that user. A GUI made available to a user, possibly after requesting a user access code and receiving a satisfactory access code from a user (such as at least one of the first party and the second party), via the portal may be operable to provide an information screen populated with information pertaining to one or more UAV zones 142, 144 that the user may be authenticated to use.

DISPLAYING INFORMATION VIA THE UAV. In embodiments of the UAV delivery system 100 that include at least one UAV 112, and as described above, the UAV 112 may have a UAV display 112a operable to display information. The information may include user-instructions, metrics associated with the UAV 112 such as a current battery level, a date and possibly time for a next scheduled maintenance, and other information such as current weather and weather forecasts at one or more UAV zones 142, 144.

In some embodiments, the display 112a may be operable with the computing system 104 of the UAV delivery system 100 to display a video feed from one or more UAV zones 142, 144, such as a delivery destination UAV zone 144. The one or more video feeds may be configured to display a condition of the UAV zone(s) 142, 144 corresponding to each feed.

LANDING IDENTIFIER. In a further aspect, one or more UAV zones 142, 144, may include a landing identifier 224. UAVs 112, including the at least one UAV 112 that may in some cases be part of the UAV delivery system 100, may be operable with at least one of the computing system 104 and the flight management system 147 to identify the landing identifier 224 at least during an approach 134 of a given UAV 112 to a given UAV zone 142, 144, and to land at or in proximity to the landing identifier 224. The flight management system 147, while shown separately may be provided on the computing system 104. The landing identifier 224 may be any suitable identifier recognizable by UAVs 112 operable to identify and land at the identifier. In yet a further aspect, the pad 226 of each of the one or more UAV zones 142, 144 may be portable. The portable pad 226 may include the landing identifier 224.

Alternatively, for some destination locations, it may be preferred or possible to avoid landing the UAV 112. Instead, the UAV 112 may hover over the UAV zone 144 at a destination, and lower a delivery article by a cable or the like. This can simplify the requirements of the landing zone at the destination, which then does not have to provide for an actual landing of the UAV, but only for landing of the delivery article.

At both delivery and destination locations, the UAV zones may be provided on a moving vehicle or otherwise be movable. For example, the vehicle could be a truck with a flat bed, a railway car, or on a ship. At least for delivery, the UAV 112 may not need to actually land, but could hover while an article is delivered by a cable or the like, as mentioned above. Where the UAV does not land, a camera is activated to film or photograph the delivery, as proof of delivery.

Further, as detailed in applicant's copending application . . . , it is possible that a UAV can be equipped to facilitate landing in any suitable location that may not be assigned or marked as a UAV landing and takeoff zone. For example, the UAV may be equipped with lights, both to make the UAV clearly visible to bystanders, even when landing in low light conditions, and to illuminate a landing zone. The illumination may be such as to define and make clear to bystanders where the UAV will be landing. This can optionally be accompanied by audio transmissions from the UAV, which may be either a simple warning noise or siren, as for other emergency vehicles, and/or an audio instruction such as; "UAV landing, please stand well back from illuminated landing area".

LANDING VIA COMPUTING SYSTEM. The computing system 104 may be operable with the executable instructions to perform at least a landing 134, 232 of a UAV 112 at a UAV zone 142, 144. Such a UAV zone 142, 144 may include the identifier device 206 operable with the computing system 104 to detect an approach and landing 134 of the UAV 112 and to record a video of the approach and landing 134. In a further aspect, a UAV 200 may include at least one sensor 210 operable with the computing system 104 to detect an approach to and landing of the UAV 200 at a UAV zone 142, 144, and to record a video of the approach and landing. For this purpose, the UAV 112 may have a sensor for identifying the landing identifier; e.g. if the landing identifier is a QR code, then the UAV 112 may have a camera, QR reader, etc. A video sensor (camera) on the UAV can record footage while the UAV is in flight to create a proof of delivery document.

MONITORING ARTICLE SAFETY. In embodiments where the UAV delivery system 100 comprises at least one UAV 112, 200, the UAV 112, 200 may be operable to engage at least one delivery article 118, 204 and may include at least one sensor 218 mountable to the delivery article 118, 204. The sensor 218 may be operable with at least one of the computing system 104 and a processor associated with that UAV 112, 200 to sense at least one of: a) forces applied to the delivery article 118, 204, and b) acceleration of the delivery article 118, 204.

The computing system 104 may be operable with the executable instructions to perform at least one of: a) provide for the viewing, for example via the portal, of the forces and acceleration applied to the at least one delivery article 118, 204, in at least one of: real-time, near real-time, and at custom time intervals; b) record a time plot of the forces and acceleration and provide the time-plot for at least one of review and download, for example, via the portal; and c) identify a maximum force and a maximum acceleration in the forces and acceleration, respectively, and provide the maximum force and acceleration for at least one of review and download, for example, via the portal.

PLOTTING FORCES AND ACCELERATION. In a further aspect, the computing system 104 may be operable to determine at least one safe range of the forces and acceleration that may be applied to, and to provide the range for at least one of: review, download, and analysis via, for example, the portal. In one example, the computing system 104 may be operable to plot a history of forces and acceleration applied to the at least one delivery article 118, 204 against the at least one safe range of the forces and acceleration. In one aspect, the computing system 104 may be operable to determine and indicate to a user (such as a customer), for example via the portal, times at which and the magnitudes by which at least one of the forces and acceleration applied to the delivery article 118, 204 during the article's 118, 204 delivery may have exceeded a safe range.

DOCUMENTING SAFE DELIVERY. In some implementations of the UAV delivery system 100, it may be desirable to record at least one form of proof of at least one aspect of the delivery of the delivery article 118, 204. In some examples, a UAV zone 142, 144, may include at least one identifier device 206 operable with the computing system 104 to detect and record an approach and landing 134, 232 of a UAV 102 at the UAV zone, and to record a video of the approach and landing 134, 232.

AN EXAMPLE METHOD. An example of a method for providing a UAV delivery service is described, for delivering an emergency or first responders' package, usually a medical package, to the scene of an accident or medical emergency.

Figure 3:
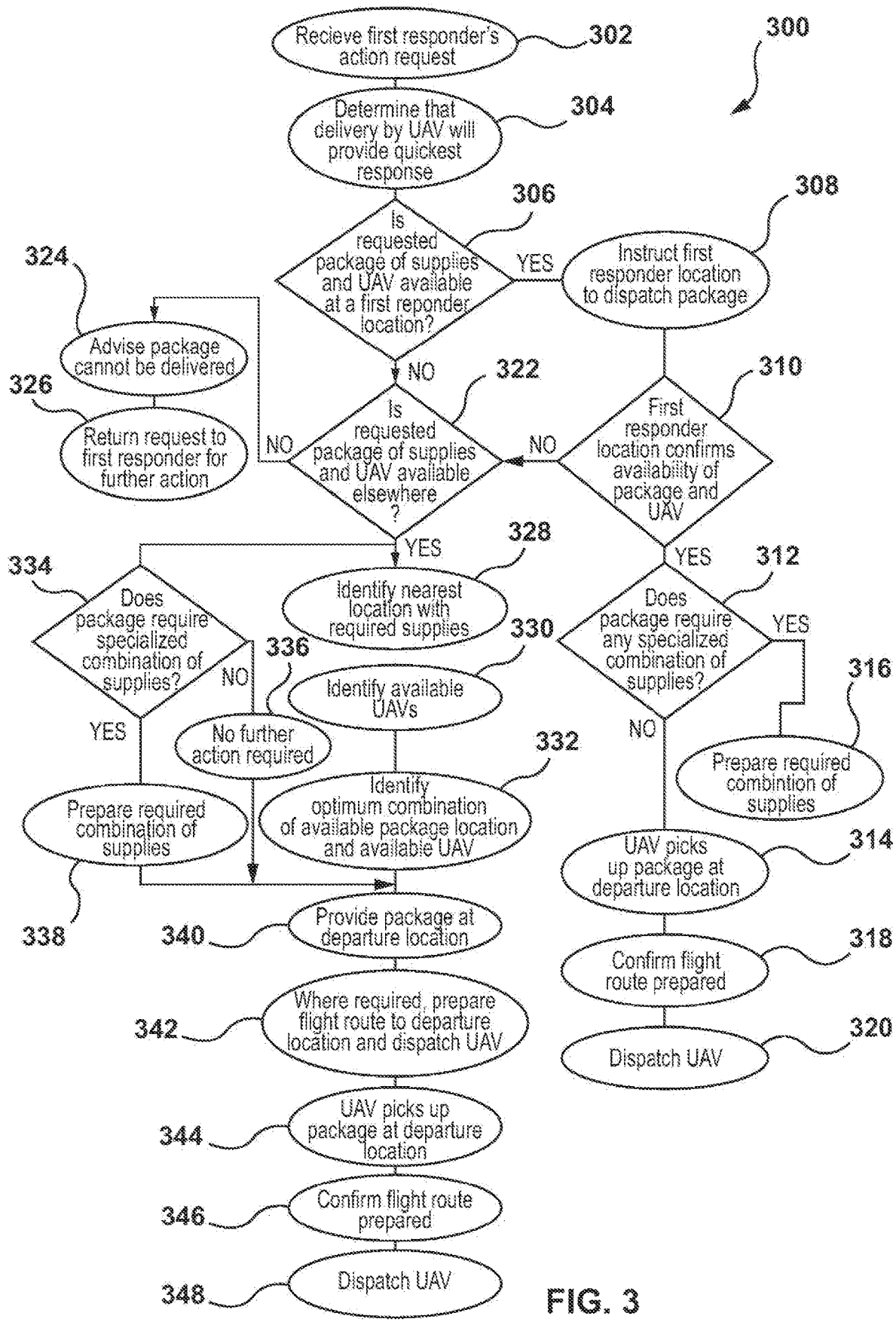
FIG. 3 is flow chart showing steps in response to a request for first responders' action.

Referring to FIG. 3, there is shown a flow chart for responding to a request from a first responder, the overall flow chart being indicated at 300. At step 302, a request is received from a first responder, for dispatch of an emergency equipment or package to the site of an emergency. For example, in case of vehicle accidents, industrial accidents and the like it may often be that the quickest way to deliver a first responders' package by a UAV.

Accordingly, a first step 304 is to determine that a delivery by a UAV will provide the quickest response. This can include checking locations of UAVs and required emergency first responders' packages, and calculating delivery times.

At step 306, a decision is made as to whether a requested first responders' package of supplies and a UAV are available at a first responder location or similar. It is anticipated that certain first responder locations, such as ambulance locations, fire halls, and also public buildings, e.g. town halls, community centers, libraries, etc. may have a specialized UAVs and emergency first responders' packages available to respond to such a request.

At 308, if such a UAV and a first responders' package are available, then the appropriate location will be instructed to dispatch the package.

Bearing in mind that while a central database in a Flight Management System, such as a Flight Management System 147 may include records of availability of UAVs and emergency packages, in practice, such records may not be wholly current. In particular, if the times between uses of UAVs and emergency packages are relatively large, there is the possibility that any one UAV and/or package may be inoperative or unavailable, and for a medical response package it is possible that it may have passed its expiry date. Accordingly, at 310, the first responder in other location either confirms the availability of the package and the UAV or advises that it cannot be provided.

At 312, if the advice is that the UAV and emergency first responders' package are available, a check is made as to whether any specialized combination of supplies is required. Here, it is expected that, to keep the weight of the package reasonable, it may be provided with only supplies anticipated as being necessary for the immediate emergency situation. For example, if the indication is that a person has suffered a heart attack, then an AED (automated external defibrillator) can be provided; if the indication is that a person is suffering a severe allergic reaction, then an appropriate drug can be included. The emergency package can also be provided with standard supplies, and if the instruction is that the standard packages to be provided, then the flow chart proceeds to 314. If a specialized package is required, then the flow chart proceeds to 316, and the appropriate supplies are provided to the package, and as detailed below, this may require particular supplies to be provided in particular compartments.

With the package prepared, the next step is to confirm that a flight route is prepared. With the flight route prepared, then at 320, a UAV with attached first responders' package is dispatched to the site of the emergency.

Returning to the top of the flow chart in FIG. 3, if, at step 310, the indication is that the combination of a UAV and necessary emergency package is not available, then, at step 322, a decision is made as to whether the requested package or supplies is available elsewhere. If the supplies are not available elsewhere, then an indication is reported at 324 and the request is returned to the first responder at 326, who will then have to determine an alternative way to deliver the requested emergency first responders' package to the site of the emergency.

Where a requested emergency package is available elsewhere, then at step 328, the nearest location with the required supplies is identified. At 330, available UAVs are also identified, and these may or may not be at the same location as the required emergency package. Practically for both step 328 and 330, the method may require identifying a number of locations of the UAVs, particularly where they are at separate locations. Then at step 332, a calculation is made as to the optimum selection of a UAV and required emergency supplies, primarily to give the quickest delivery times to the emergency site. Additional factors can be taken into consideration. For example, in the event of an extreme and localized weather condition, at one location, it may be determined not to use a UAV at that location, even if it would otherwise give a shorter delivery time; if there are different types of UAVs available, they may provide different speeds and flight times. The selection of UAVs may also include selection from UAVs already assigned to missions and even UAVs in flight; if necessary, selection of such a UAV will require its current mission to be aborted, and the UAV assigned to the emergency delivery.

As indicated, in parallel with the steps 328 to 332, as for the steps 312 to 316, a determination is made at 334, if the emergency package requires a specialized combination of supplies. As indicated at 336, if no specialized supplies are required, then no change is made to the package. Alternatively, at 338, if a specialized combination is required, then at 336, the necessary combination of supplies is made up.

If the emergency package is provided at a departure location and the UAV is available at the same location, then the package is attached to the UAV.

Alternatively, as indicated at 342, where a UAV is at a separate location, this is dispatched to the departure location to pick up the package, as indicated at 344.

Again, at 346, after a flight route is confirmed and after the UAV has picked up the package or has been attached to the package, then the UAV with the attached package is dispatched at 348.

Figure 4:
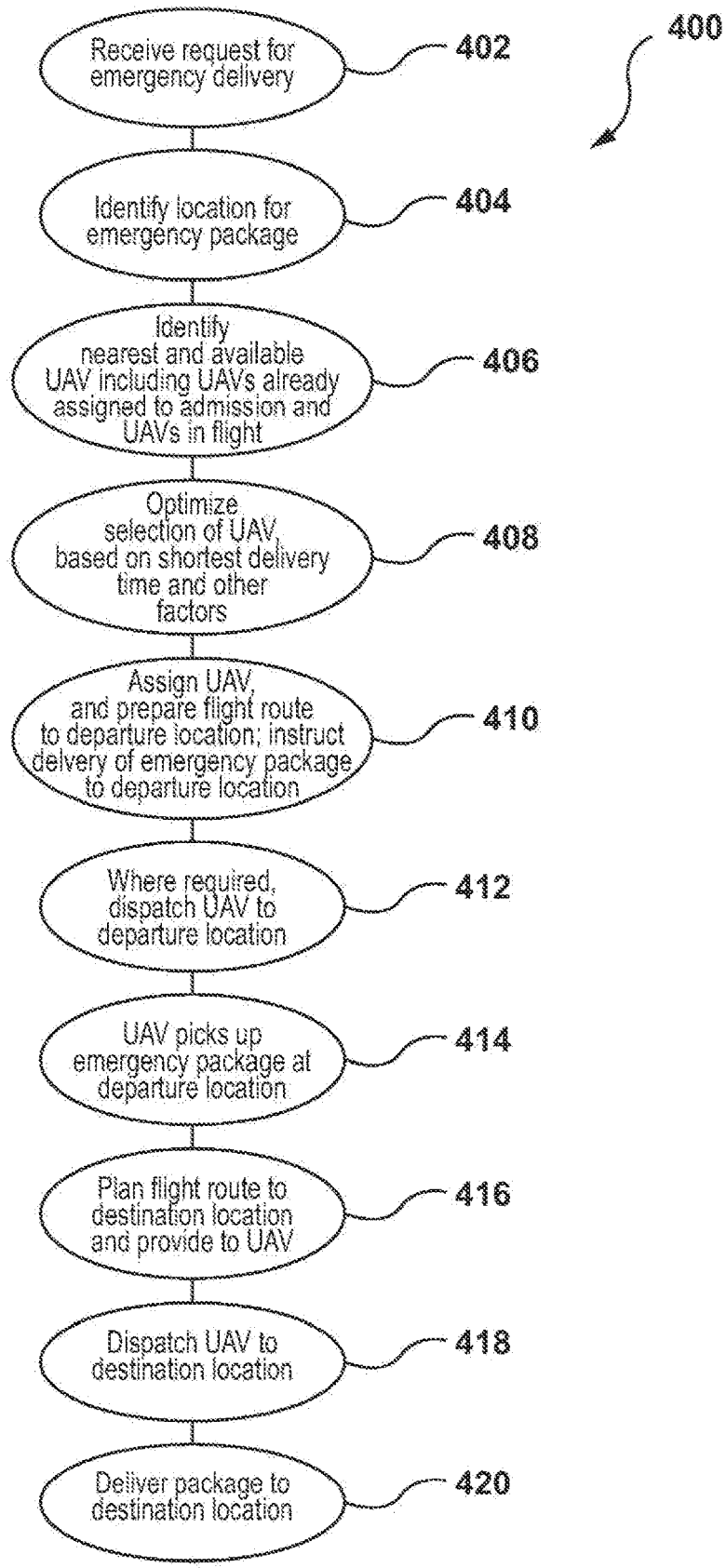
FIG. 4 is a flow chart showing steps in response to request for delivery of an emergency package.

Referring to FIG. 4, this shows a flow chart for delivery on a rush or emergency basis of an article, that may be entirely separate from any first responders' package or request. For example, a physician or a hospital may request a rush delivery of a particular drug to an individual.

A flow chart is indicated at 400, and as indicated at 402, the flight Management System 147 would receive a request for an emergency delivery. At 404, the location of the emergency package would be identified. Generally, for simplicity and to fit within the existing flight route network, the package should be delivered to an existing UAV Zone 142, 144. In some circumstances, it may be necessary or possible to pick up a package from a location or a zone not part of the route network, for example, at a hospital.

With the location for the pick-up of the package identified, at 406, the Flight Management System 147 would identify the nearest and available UAV. For this purpose, the Flight Management System 147 may include UAVs already assigned to delivery missions, and possibly UAVs already in flight. When necessary these assigned or in progress missions will be aborted, and the selected UAV will be directed to the pick-up location for the package. As indicated at 408, the selection of the UAV can be based on delivery times and other factors.

At 410, a UAV is assigned and a flight route to the departure location is prepared. As indicated, where necessary, instructions are provided to the person requesting the delivery to deliver the emergency package to the selected departure location.

At 412, where required, the UAV is dispatched to the departure location, if not already present at that location. At 414, the UAV arrives at the departure location and picks up the emergency package. At 416, a flight route is planned to a destination location and provided to the UAV. Step 416, can be carried out in parallel with earlier steps selection of the UAV, etc. At 418, the UAV is dispatched to the destination location and at 420 arrives to deliver the package.

Figure 5:
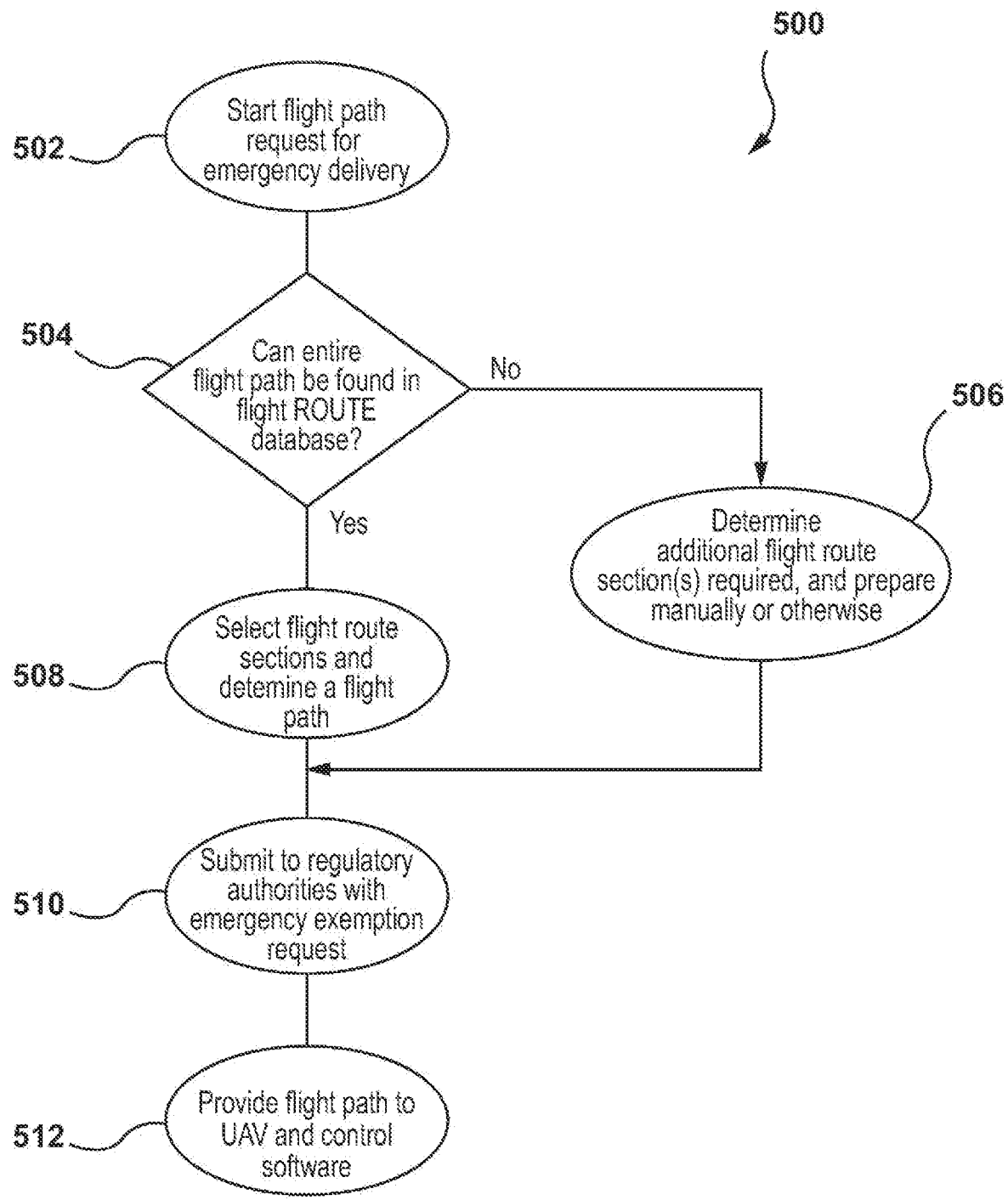
FIG. 5 show steps in a method to prepare a flight path for delivery of an emergency package.

FIG. 5 shows a flow chart for determining for an emergency requested flight path, the flow chart being indicated at 500.

At 502, a request is made for the preparation of a flight route for an emergency delivery. At 504, a check is made as to whether the entire flight route can be found in the flight database. If the answer is no, then at 506, additional flight route extensions are required and prepared. If necessary, these are prepared manually. Unlike preparation of a flight routes for a conventional, non-emergency delivery, Rules and Regulations may permit selection of route extensions that otherwise may not be permitted. For example, conventional route planning may require that the UAV maintain certain distances with respect to highways, particularly major highways. If the emergency request is to deliver a package of an emergency supplies to scene of a highway accident, then necessarily this Rule cannot be followed.

At 508, if the entire route can be determined from route sections in a database, then the appropriate flight route is determined. At 510, the route network would be submitted to Regulatory authorities for approval, if it is not comprised of a flight route that is already been approved. Where a flight route includes a route extension, not in the database, then, for a normal delivery, Regulations may require that prior approval be obtained; for an emergency delivery, Regulations may provide that no prior approval be required, and may require reporting only if the route extension Alternatively, Regulations may provide that, for an emergency delivery, approval is provided on a "negative option" basis. In other words, the route is submitted, and no rejection is received within a set, short time, the submitter can determine that the flight route has been approved. Regulations may also provide that such a rule applies to short route extensions that are not in any database; limitations may be provided, e.g. such a route section must be below a certain maximum and must avoid certain prohibited areas, e.g. an airport. This could be used to establish the last route extension to reach the scene of a highway accident.

At 512, the flight route is provided to the UAV, control software and the Flight Management System 147.

Where a UAV is in flight delivery an emergency or medical package, or other priority package, the Flight Management System 147 may control UAVs along the route to ensure that the UAV with the emergency or priority package is not delayed. If necessary other UAVs can be diverted or required to land for short periods of time to allow the priority UAV to pass.

Figure 6A:
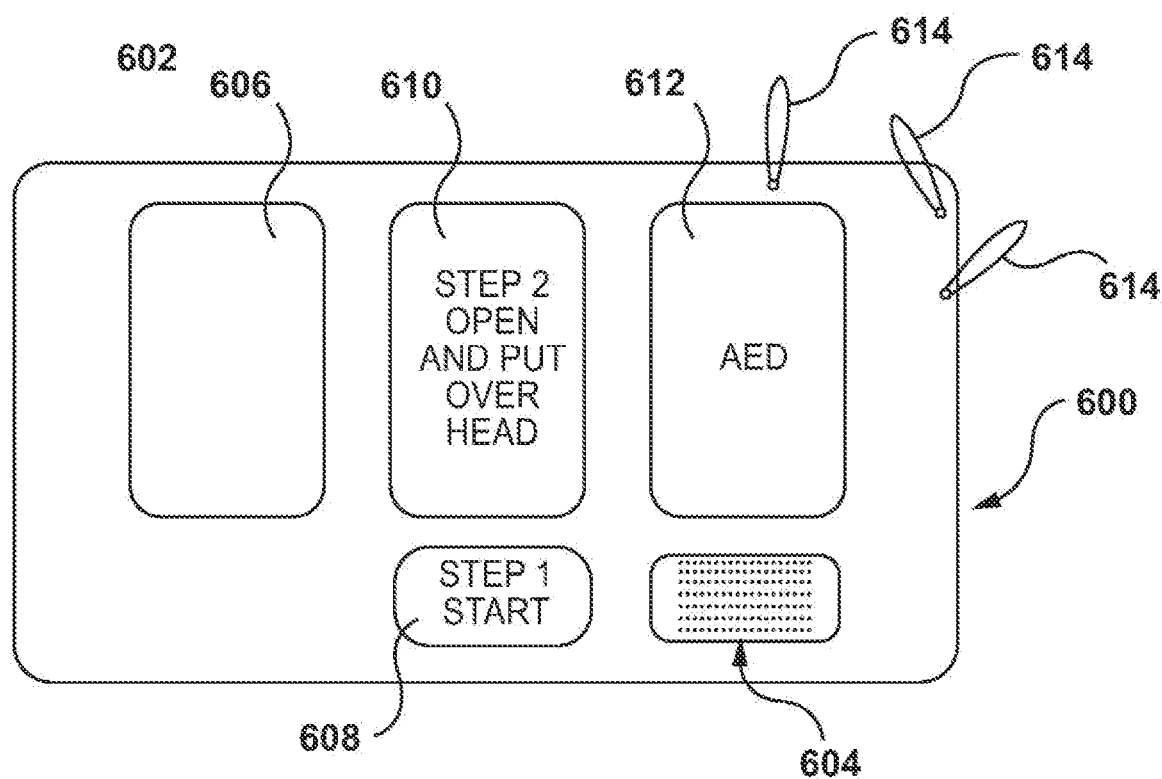
FIGS. 6A and 6B show a top view and a side view of a responders' package for delivery by a UAV.
Figure 6B:
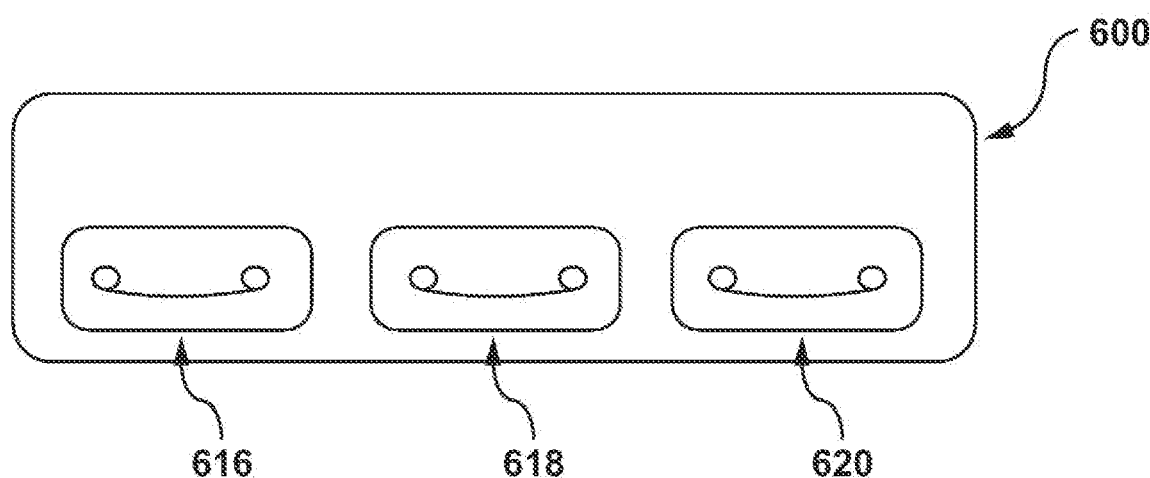

Reference is now made to FIGS. 6A and 6B which show an exemplary emergency package, indicated at 600. The Package 600 may include a body 602 formed from a light but impact resistant material, for example, fiber reinforced plastic. The body 602 may be provided with a high visibility finish and may be waterproof.

The package 600 includes a speaker 604 and a display screen 606 for displaying instructions.

The package 600 may include a start button indicated at 608, which may be provided with a sharp contrasting colour relative to other elements, to draw users' attention to it. At 610, there is a compartment enclosing a headset to be worn by a user. At 612, there is a compartment that can include an automated external defibrillator (AED). As indicated at 614, various antennas can be provided, for example for GPS communication, cellular communication and for communication to a headset contained in the compartment 610.

A side view of the package 600 is shown in FIG. 6B, indicating compartments or doors 616, 618, 620.

Figure 7:
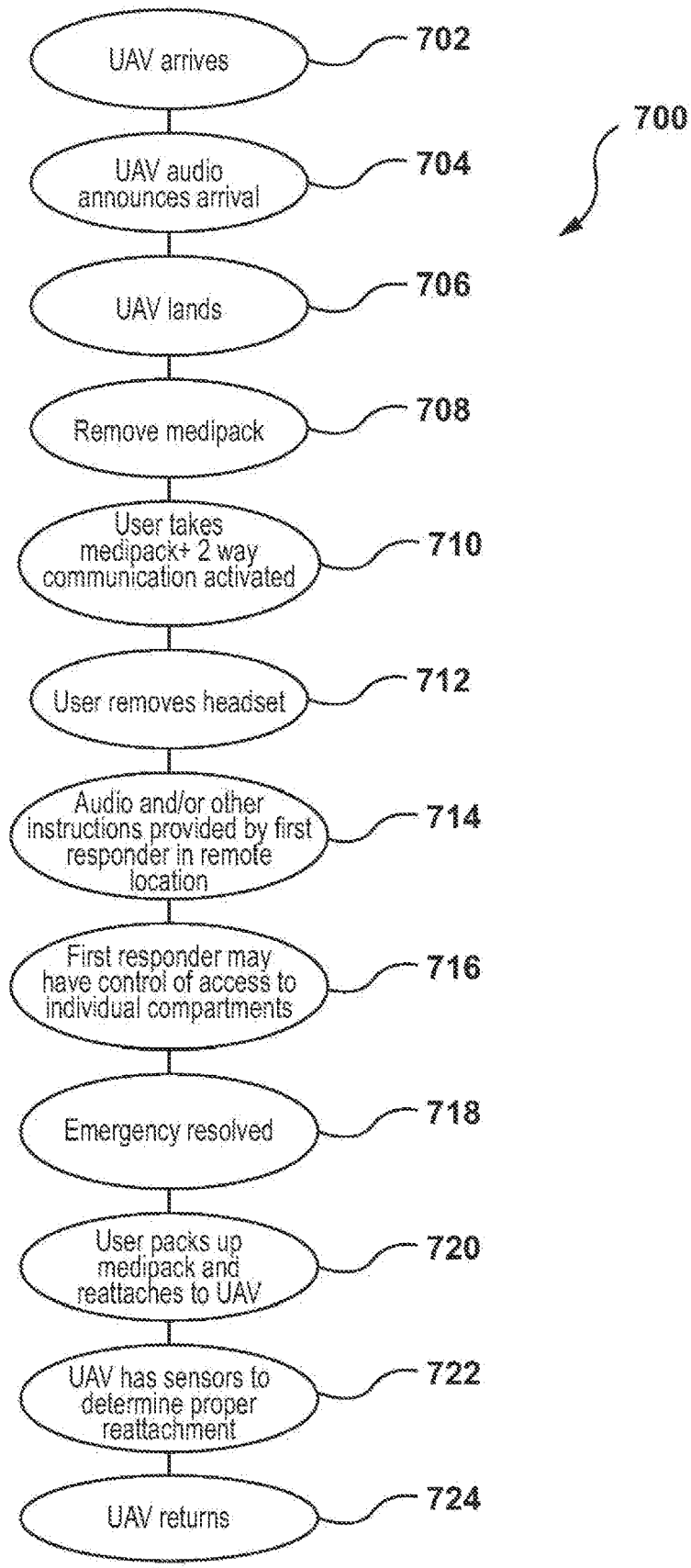
FIG. 7 shows steps in a method of use of the package of FIG. 6.
Figure 8:
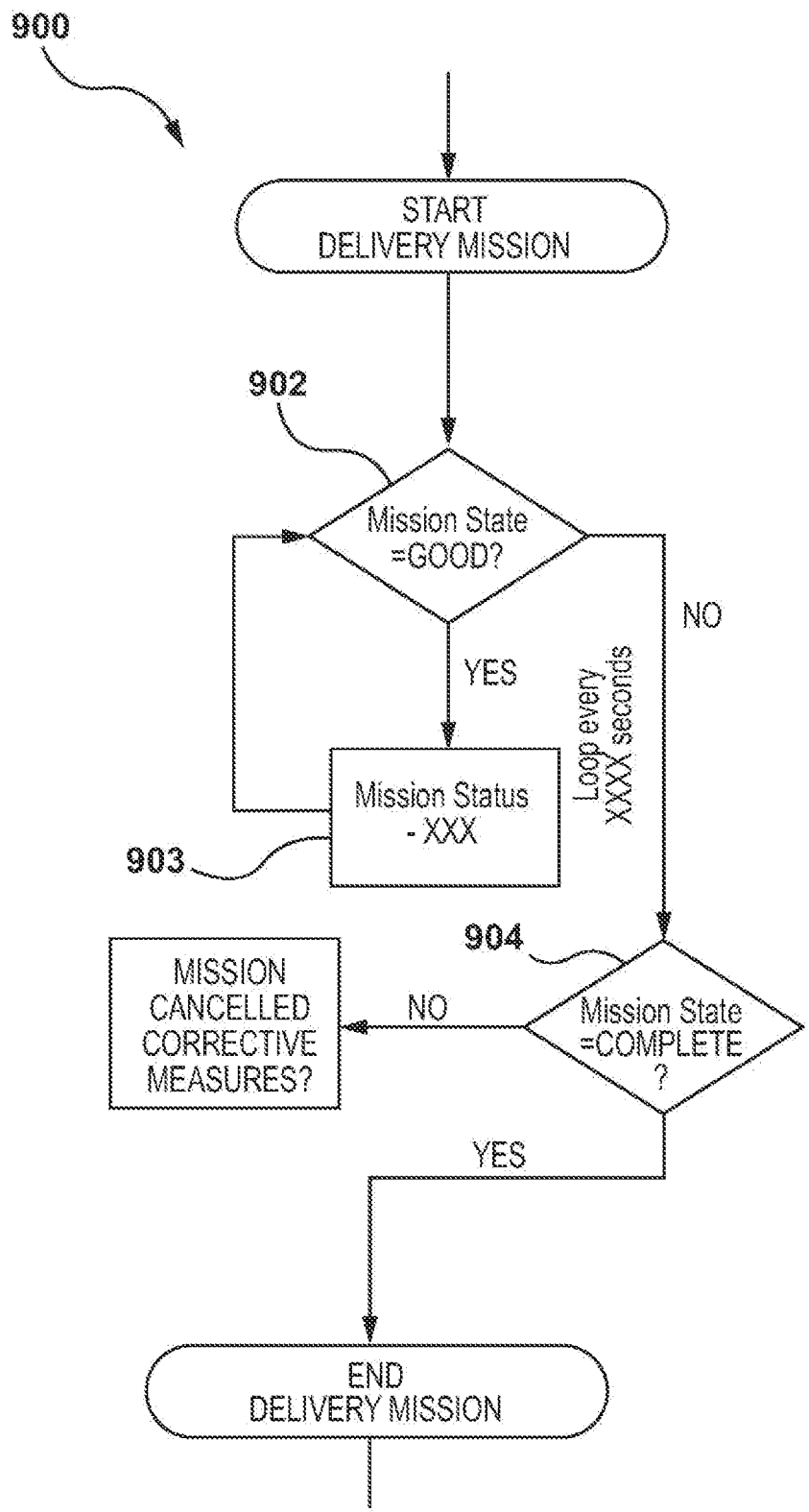
FIG. 8 shows steps in completing a delivery mission for delivery of emergency package.
Figure 9:
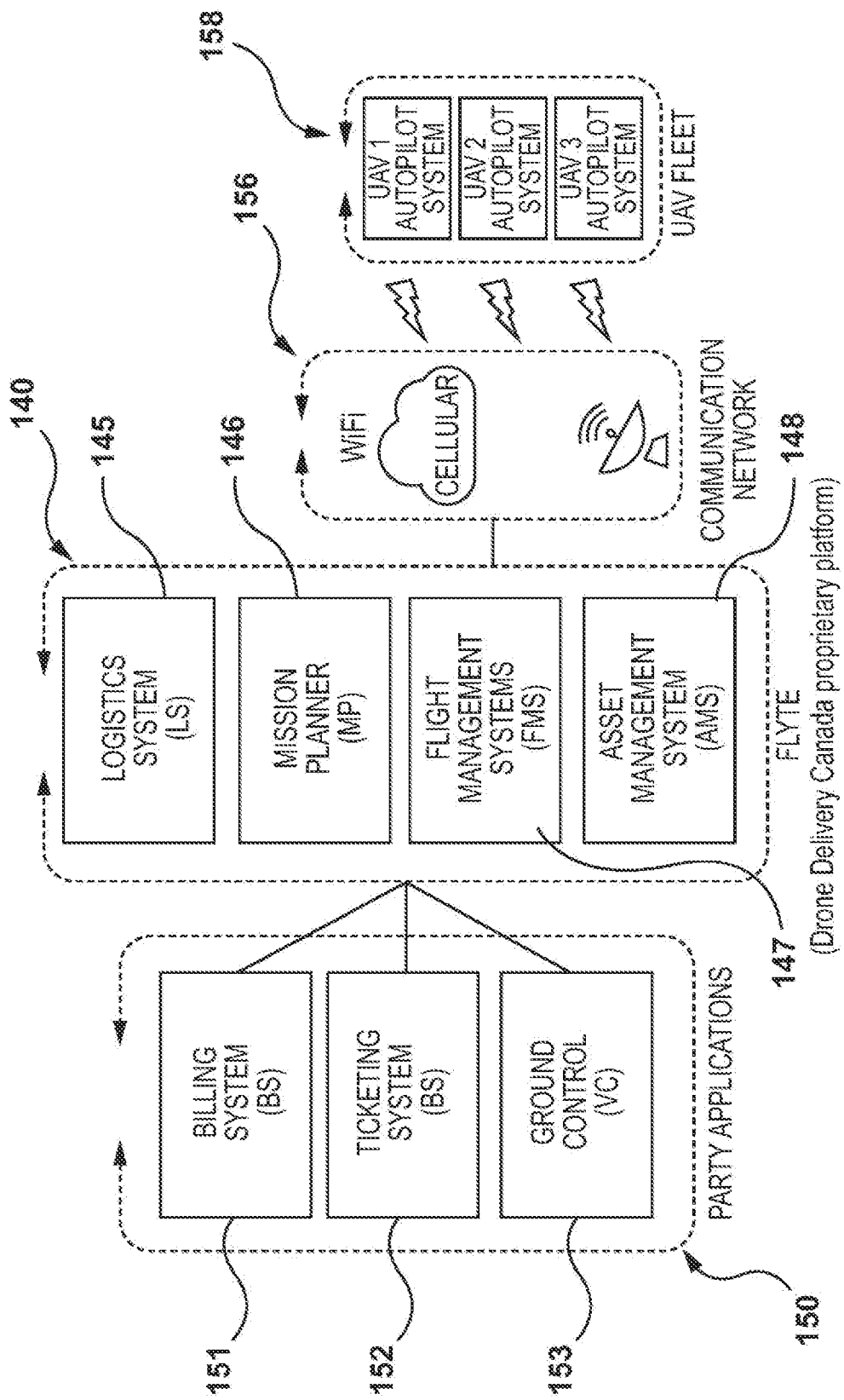
FIG. 9 indicates elements in a UAV control platform, including third party applications; communications network and the UAV fleet.

Referring to FIG. 7, is shown a flow chart for operation of the emergency responders' package 600, shown in FIGS. 6A and 6B, the flow chart being indicated at 700.

As indicated in 702, a UAV arrives to deliver the first responders' package 600. At 704, and as required, an audio announcement can be made to clear a landing area for the UAV, at the scene of an accident or emergency. This can be provided either by the UAV, if it has the necessary capability, or it can be included in the package 600.

At 706, the UAV lands and the first responders' package or medipack 600 is detached from the UAV.

At 710, a user at the scene commences to use the first responders' package 600. It is anticipated that in many instances, the package 600 will be delivered to the scene of an accident, where it will be used by an untrained, lay person with no medical or other skills. Accordingly, the first responders' package 600 may be designed with this in mind, and, as detailed below, may provide for a trained and qualified first responder at a location remote from the accident scene to have varying degrees of control and input on actions taken at the emergency scene.

First, the package 600 includes the start button 608. A user will press this button, and this will open the compartment 610. This action will cause the user to be provided with audio instructions, either automatically or from a remote first responder, to remove a headset from the compartment 610 and place the headset on the user's head.

The headset can include both earpieces for the user and a microphone so the user has voice communication with a remote first responder; the microphone, or additional microphone(s) can be provided to pickup all ambient audio. The headset may also include a camera, so a remote, first responder will have essentially the same eye view of the emergency scene as the user. The intent is to provide the remote, first responder with the same audio and visual information as the user at the scene of the accident or emergency.

It is also possible that the remote, first responder could be given control over operation of the camera, to at least some degree. For example, if the camera has a zoom function, the remote first responder can control the zoom so as to obtain a view useful to that first responder.

It is also possible that other equipment could be provided, while recognizing that, in many emergency situations simplicity and quick response will be essential. For example, a second camera could be provided on a tripod or a stand, for a user to position close to an accident scene to provide a view point useful to a first responder, without movement imparted by a camera mounted on a headset.

The compartment 610, or a separate compartment, may also include equipment for measuring vital signs of a person who may be injured. If so, the compartment may also include written instructions for use of this equipment. Additionally, a first responder can provide audio instructions to a user, for attaching the vital signs measuring equipment to an injured person. In known manner, the vital sign measuring equipment may measure blood pressure, pulse, and temperature at least. Vital signs usually also include respiratory rate, and a user at the scene may be instructed by the remote, first responder to measure the respiratory rate, e.g. by simply counting number of breaths in a certain time period; for this purpose, if necessary, the equipment can include a simple timing device or stop watch.

Thus, the step includes attaching the vital signs measuring equipment to an injured person. Further, the vital signs measuring equipment can be connected to the package 600, wirelessly or otherwise, to transmit data back to a remote first responder. It is recognized that in some situations, the treatment needed for an injured person will be immediately apparent, even to an untrained person. Alternatively, recognizing that it will take a finite time, even for a closely located UAV to deliver the emergency package, a user attending an injured person may already have been in contact with a first responder by a telephone or otherwise, and, between them, it may have been determined what action is immediately required. For example, if an injured person has a severe cut and bleeding that immediately requires that the application of a tourniquet, then it is not necessary to take time making any other assessment. Similar consideration applies, if it is immediately apparent that a person is having a heart attack; in this case, immediate application of the AED is required, and further evaluation will not be required.

In other situations, some assessment may be required, and it may often be necessary for a remote first responder to gather as much information as possible, to make a determination on treatment to be applied.

For this purpose, the first responder can provide instructions to a user at the scene, either through the audio link, or by text or otherwise. Simultaneously, the user at the scene can, also using the audio link, text or otherwise, communicate back to the first responder. Where vital signs measuring equipment has been used, this can provide data directly back to the first responder. The user at the scene can also provide further information on the condition of the injured person, e.g. state of consciousness, respiratory rate, indications of bruising, and obvious external indications of injuries. A user at the scene may also be able to obtain useful information from the injured person, if the person is conscious, concerning, for example, drugs, alcohol, etc. that the person has consumed. Based on this information, the first responder can determine the necessary course of action and treatment. For this purpose, the compartments 616, 618 and 620 may be locked and access controlled by the remote first responder. Having determined a desired action or treatment, the first responder can unlock or permit access to the appropriate compartment. For example, if an injured person is suffering an allergic reaction, access can be provided to a compartment containing an epinephrine autoinjector. Alternatively, if it is apparent that the injured person is suffering a heart attack, access to the AEC is enabled; if it is apparent or determined that the person is suffering from a stroke, access to a compartment containing a clot dissolving drug can be provided.

At 718, if the emergency has been resolved or the user of the scene has provided whatever treatment is possible using the first responders' emergency package, then no further action is taken. Alternatively, the sequence may end, when first responders are able to attend directly at the scene of the emergency.

Desirably, although it is recognized this may not occur in all instances, at 720, a user repacks the equipment into the package 600, and attaches the package 600 to the UAV, as indicated at 720. At 722, the UAV has sensors to determine proper reattachment of the package 600. Once confirmed, the UAV can return as indicated at 724.

Alternatively, in many situations, if first responders arrive directly at the scene of the emergency after the user has provided some initial action and treatment, then the first responders may retrieve both the package 600 and the UAV, for return.

While the above description provides examples of one or more apparatuses or methods, it will be appreciated that other apparatuses or methods may be within the scope of the accompanying claims. Additionally, while certain combinations of features, elements and method steps are claimed in the accompanying claims, it is to be understood that any practical combination of these features, elements and method steps is envisaged and is part of the present disclosure.

The invention claimed is:

1. An emergency or medical package comprising:
a body;
attachment fittings, for attachment to complementary fittings of an Unmanned Aerial Vehicle (UAV) for delivery of the package by the UAV to a destination location; and
a plurality of compartments for housing medical or emergency supplies, including a compartment for a headset to be worn by a user, the headset providing for two-way audio and visual communication between a user of the headset at the destination location and a remote person, the remote person being remote from the package,
the plurality of compartments including a plurality of locked compartments and providing each locked compartment with medical equipment for a particular medical emergency, each locked compartment being openable only by the remote person, whereby the remote person can open each selected locked compartment independently based on the particular medical emergency to permit access to the medical equipment contained therein such that a first locked compartment of the plurality of locked compartments is unlockable by the remote person in response to determining a first course of treatment, the first locked compartment containing medical equipment for performing the first course of treatment; and a second locked compartment of the plurality of locked compartments is unlockable by the remote person in response to determining a second course of treatment, the second locked compartment containing medical equipment for performing the second course of treatment.

2. The emergency or medical package as claimed in claim 1, wherein the headset communicates wirelessly with the package, and the package includes wireless communication, directly or indirectly, with the remote person.

3. The emergency or medical package as claimed in claim 1, wherein the package additionally includes vital signs measuring equipment for measuring at least one of a person's pulse, blood pressure and temperature, and for transmitting data from those measurements to the remote person.

4. The emergency or medical package as claimed in claim 3, wherein the vital signs measuring equipment communicates with the package.

5. The emergency or medical package as claimed in claim 4, wherein the vital signs measuring equipment additionally include sensors for measuring respiration rate and an blood oximeter measuring blood oxygen levels.

6. The emergency or medical package as claimed in claim 1, wherein at least one of the locked compartments can only be opened by a signal sent by the remote person, to enable the remote person to have control of access to at least some of the medical supplies.

7. The emergency or medical package as claimed in claim 6, wherein the plurality of locked compartments are provided with at least one of:
an automated external defibrillator;
an epinephrine autoinjector; and
a clot-dissolving drug.

8. The emergency or medical package as claimed in claim 1, wherein the headset includes a camera mounted to show the same view as the user of the headset and including microphone to pick up ambient sounds, whereby the remote person is provided with substantially the same audio and visual information as the user.

9. The emergency or medical package as claimed in claim 8, wherein the camera on the headset is provided with adjustable functions, included at least a zoom function, remotely operable by the remote person.

10. The emergency or medical package as claimed in claim 1, wherein the UAV is provided with a light source for illuminating and indicating a landing zone below the UAV, as the UAV descends and lands.

11. The emergency or medical package as claimed in claim 10, wherein the UAV is provided with at least one of another light source and an audio source, to warn bystanders of the approach and landing of the UAV.

12. The emergency or medical package as claimed in claim 1, wherein the attachment fittings are mounted on arms of the UAV.

13. The emergency or medical package as claimed in claim 1, wherein at least one of the attachment fittings and complementary fittings comprise a sensor to detect correct attachment of the package to the UAV.

14. The emergency or medical package as claimed in claim 1, further comprising a speaker and a display screen for displaying instructions of the remote person.

15. The emergency or medical package as claimed in claim 1, wherein the headset is provided in one of the unlocked compartments of the package.

16. The emergency or medical package as claimed in claim 1, further comprising a start button on the package to initiate the use of the package by actuation of the start button by the remote person.

17. The emergency or medical package as claimed in claim 16, wherein actuation of the start button causes an unlocked compartment containing the headset to open to present the headset to the remote person and to cause instructions for use of the headset to be provided to the remote person.

18. The emergency or medical package as claimed in claim 1, wherein the body is formed from a light but impact resistant material.

19. The emergency or medical package as claimed in claim 18, wherein the body is formed from a fiber reinforced plastic material.

20. The emergency or medical package as claimed in claim 1, wherein the body is formed from a waterproof material.

* * * * *